(12) United States Patent
Peeters et al.

(10) Patent No.: US 7,413,706 B2
(45) Date of Patent: Aug. 19, 2008

(54) REPLACEABLE PARYLENE MEMBRANES FOR NANOCALORIMETER

(75) Inventors: Eric Peeters, Fremont, CA (US); Gregory B. Anderson, Woodside, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 738 days.

(21) Appl. No.: 10/741,635

(22) Filed: Dec. 19, 2003

(65) Prior Publication Data

US 2005/0135455 A1 Jun. 23, 2005

(51) Int. Cl.
*C12Q 1/68* (2006.01)
*G01N 33/00* (2006.01)
*G01N 15/06* (2006.01)
*G01N 33/48* (2006.01)
*G01K 17/00* (2006.01)

(52) U.S. Cl. .......................... 422/50; 422/51; 422/68.1; 436/43; 436/147; 374/29; 374/31; 374/32; 374/33

(58) Field of Classification Search .................. 422/50, 422/51, 68.1; 436/43, 147; 374/29, 31, 32, 374/33
See application file for complete search history.

(56) References Cited

U.S. PATENT DOCUMENTS

| | | | | |
|---|---|---|---|---|
| 4,928,513 | A * | 5/1990 | Sugihara et al. | 73/25.03 |
| 5,012,671 | A * | 5/1991 | Yagawara et al. | 73/31.06 |
| 5,451,371 | A * | 9/1995 | Zanini-Fisher et al. | 422/51 |
| 5,659,127 | A * | 8/1997 | Shie et al. | 73/31.05 |
| 6,193,413 | B1 * | 2/2001 | Lieberman | 374/45 |
| 6,436,346 | B1 * | 8/2002 | Doktycz et al. | 422/51 |
| 7,104,113 | B2 * | 9/2006 | Zribi et al. | 73/31.05 |
| 2003/0183525 | A1 | 10/2003 | Elrod et al. | |
| 2003/0186453 | A1 | 10/2003 | Bell et al. | |
| 2006/0018360 | A1 * | 1/2006 | Tai et al. | 374/121 |

* cited by examiner

*Primary Examiner*—Brian J Sines
(74) *Attorney, Agent, or Firm*—Bever, Hoffman & Harms, LLP; Patrick T. Bever

(57) ABSTRACT

A measurement operation, such as a calorimetry measurement, is performed using a measurement array and a replaceable passivation membrane (e.g., a parylene membrane). The passivation membrane is used to cover the measurement array to provide temporary electrical and chemical passivation, while still allowing measurement of the parameter of interest (e.g., temperature, in a calorimetry measurement). By only replacing the membrane instead of the entire measurement array between measurement operations, the cost of the measurements can be significantly reduced over conventional methods. The passivation membrane can be mounted on a frame to simplify handling of the membrane.

8 Claims, 6 Drawing Sheets

REPLACEABLE PARYLENE MEMBRANES FOR NANOCALORIMETER

BACKGROUND OF THE INVENTION

1. Field of the Invention

The invention relates to the field of calorimetry, and in particular, to a system and method for reducing nanocalorimetry operating costs.

2. Related Art

Calorimetry is used to measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced.

For example, measurements of enthalpy as a function of temperature reveal the heat capacity of a specimen, and titrations of reacting components can be used to deduce the binding constant and effective stoichiometry for a reaction. Calorimetry measurements are useful in a broad variety of applications, including, for example, pharmaceuticals (drug discovery, decomposition reactions, crystallization measurements), biology (cell metabolism, drug interactions, fermentation, photosynthesis), catalysts (biological, organic, or inorganic), electrochemical reactions (such as in batteries or fuel cells), and polymer synthesis and characterization, to name a few.

In general, calorimetry measurements can be useful in the discovery and development of new chemicals and materials of many types, as well as in the monitoring of chemical processes. Standard calorimeters require relatively large samples (typically about 0.5 ml to 10 liters) and usually measure one sample at a time. As such, these systems cannot be used to measure very small samples, as might be desired for precious or highly reactive materials. Furthermore, standard calorimeters cannot be used effectively to monitor a large number of reactions of small sample size in parallel, as is required in order to perform studies using combinatorial chemistry techniques.

In recent years, researchers and companies have turned to combinatorial methods and techniques for discovering and developing new compounds, materials, and chemistries. For example, pharmaceutical researchers have turned to combinatorial libraries as sources of new lead compounds for drug discovery. As another example, Symyx Technologies™ is applying combinatorial techniques to materials discovery in the life sciences, chemical, and electronics industries.

Consequently, there is a need for tools that can measure reactions and interactions of large numbers of very small samples in parallel, consistent with the needs of combinatorial discovery techniques. Preferably, users desire that these tools enable inexpensive measurements and minimize contamination and cross-contamination problems.

One of the most popular uses of combinatorial techniques to date has been in pharmaceutical research. Pharmaceutical researchers have turned to combinatorial libraries as sources of new lead compounds for drug discovery. A combinatorial library is a collection of chemical compounds that have been generated, by either chemical synthesis or biological synthesis, by combining a number of chemical "building blocks" as reagents. For example, a combinatorial polypeptide library is formed by combining a set of amino acids in every possible way for a given compound length (i.e., the number of amino acids in a polypeptide compound). Millions of chemical compounds can theoretically be synthesized through such combinatorial mixing of chemical building blocks.

Once a library has been constructed, it must be screened to identify compounds, which possess some kind of biological or pharmacological activity. For example, screening can be done with a specific biological compound, often referred to as a target, that participates in a known biological pathway or is involved in some regulation function. The library compounds that are found to react with the targets are candidates for affecting the biological activity of the target, and hence a candidate for a therapeutic agent.

Through the years, the pharmaceutical industry has increasingly relied on high throughput screening (HTS) of libraries of chemical compounds to find drug candidates. HTS describes a method where many discrete compounds are tested in parallel so that large numbers of test compounds are screened for biological activity simultaneously or nearly simultaneously. Currently, the most widely established techniques utilize 96-well microtitre plates. In this format, 96 independent tests are performed simultaneously on a single 8 cm by 12 cm plastic plate that contains 96 reaction wells. These wells typically require assay volumes that range from 50 to 500 microliters. In addition to the plates, many instruments, materials, pipettors, robotics, plate washers and plate readers are commercially available to fit the 96-well format to a wide range of homogeneous and heterogeneous assays. To achieve faster testing, the industry is evolving to plates that contain 384 and 1536 wells.

A variety of measurement approaches has been used to screen combinatorial libraries for lead compounds, one of which is the inhibitor assay. In the inhibitor assay, a marker ligand, often the natural ligand in a biological pathway, is identified that will bind well with the target protein molecule. The assay requires the chemical attachment of a fluorescent molecule to this marker ligand such that the fluorescent molecule does not affect the manner in which the marker ligand reacts with the target protein. To operate an inhibitor assay, the target protein is exposed to the test ligands in microtitre wells. After a time necessary for reaction of the test ligand to the target protein, the marker ligand is applied. After a time for reaction with the marker ligand, the wells are rinsed such that non-reacted marker ligand is washed away. In wells where the target protein and the test ligand have reacted, the test ligand blocks the active site of the target protein so the marker ligand cannot react and is washed away, while in cells where the target protein and test ligand have not reacted, the marker ligand reacts with the target protein and is not washed away. By investigating the wells for the presence of fluorescence after the washing, reactions of test ligands and target proteins can be determined as having occurred in wells where no fluorescence is observable.

However, the inhibitor assay requires time and expense to develop the assay. The principal components that need development are discovering a marker ligand and attaching a fluorophore to the marker in a manner that does not affect its reaction with the target protein. Attaching the fluorescent marker can often take 3 months of development or more and cost $250 k or more once the marker ligand is identified. An assay method that avoids such assay development, such as measuring the heat of the reaction with calorimetry, would eliminate this cost and lime delay in the discovery process.

Calorimetry measurements are commonly utilized in biophysical and biochemical studies to determine energy changes as indications of biochemical reactions in a media. Prior techniques for measurements include using electrodes, thermopiles, optical techniques, and microcalorimeters for measurements within a sampled media. There is a great interest in developing calorimetry devices, and in particular, ultra-miniature microcalorimeter devices (i.e., nanocalorimetry devices), that require very small volumes of sampled media and that can quickly measure large numbers of reactions. Ideally, those reaction measurements can provide efficient assays; e.g., inhibitor assays which can be used in HTS to screen roughly 100,000 test ligands a day.

Accordingly modern calorimetry tools (in particular, microcalorimetry and nanocalorimetry tools) include an array of detectors that allow multiple measurement operations to be performed simultaneously. FIG. 1A shows a top view of a nanocalorimeter array 100, which is similar to nanocalorimeter arrays described in detail in co-owned, co-pending U.S. Patent Application Serial No. 2003/0186453, herein incorporated by reference.

Nanocalorimeter array 100 includes a frame 110 and two detectors 120. Detectors 120 are commonly amorphous silicon (a-Si) structures that are formed on a Kapton™ plastic film (shown in FIG. 1B), which in turn is supported by frame 110. Detectors 120 include the devices necessary to perform calorimetry measurements on sample droplets 190 of test material. The measurement data is then read out from detectors 120 via contacts 111 on the periphery of frame 110.

In addition, microcalorimeter and nanocalorimeter arrays, such as nanocalorimeter array 100, typically include a thin (1-3 μm) parylene coating 130 that is deposited over detectors 120 (and frame 110). Sample droplets 190 are placed directly onto parylene coating 130, which provides a hydrophobic surface that facilitates the merging and mixing of sample droplets 190. Parylene coating 130 also provides electrical and chemical passivation for detectors 120, while still allowing the thermal effects of droplet interactions to be measured by detectors 120.

The coverage provided by parylene coating 130 is more clearly depicted in FIG. 1B, which shows a cross section of nanocalorimeter array 100. As described above with respect to FIG. 1A, parylene coating 130 covers detectors 130, which in turn are formed on Kapton™ layer 131 (copper strips 132 beneath detectors 130 are isothermal elements to ensure that the measurement elements of detectors 120 are thermally coupled to sample droplets 190).

To avoid contamination, nanocalorimeter arrays (such as nanocalorimeter array 100) are typically discarded after a single use, which can add significant costs to large nanocalorimetry experiments. While parylene coating 130 can sometimes be cleaned and sterilized to enable re-use of nanocalorimeter array 100, such refurbishment activity can be time-consuming and expensive.

Accordingly, it is desirable to provide a system and method for performing calorimetry operations that enables reuse of calorimeter arrays.

SUMMARY OF THE INVENTION

By using a replaceable (removable) passivation membrane, the invention beneficially provides a simple means by which calorimeter arrays can be re-used. According to an embodiment of the invention, the passivation membrane is used to cover the uncoated measurement elements of a calorimeter array. Sample droplets are deposited onto the passivation membrane, and the calorimetry measurements are taken. Once the measurements are completed, the passivation membrane is simply removed from the calorimeter array. A new passivation membrane can then be placed over the calorimeter array to allow the next measurement operation to be performed.

Because only the passivation membrane is replaced for each new measurement operation, the invention can significantly reduce the total cost of a series of measurement operations compared to conventional single-use calorimeter arrays. According to an embodiment of the invention, the passivation membrane can be mounted on a rigid frame to facilitate placement of the passivation membrane over the calorimeter array, thereby improving measurement throughput by simplifying the replacement of the passivation membrane after each measurement operation.

According to an embodiment of the invention, the passivation membrane can be produced by depositing a thin layer of the passivation material onto a form created by a frame and a temporary backing structure mounted to the frame. A thin layer of the desired membrane material is then deposited on the exposed portions of the frame and the backing structure within the frame. The membrane layer is then released from the backing structure (via a low-adhesion film on the backing structure), leaving the membrane supported by only the frame.

DETAILED DESCRIPTION

Figure 2A:
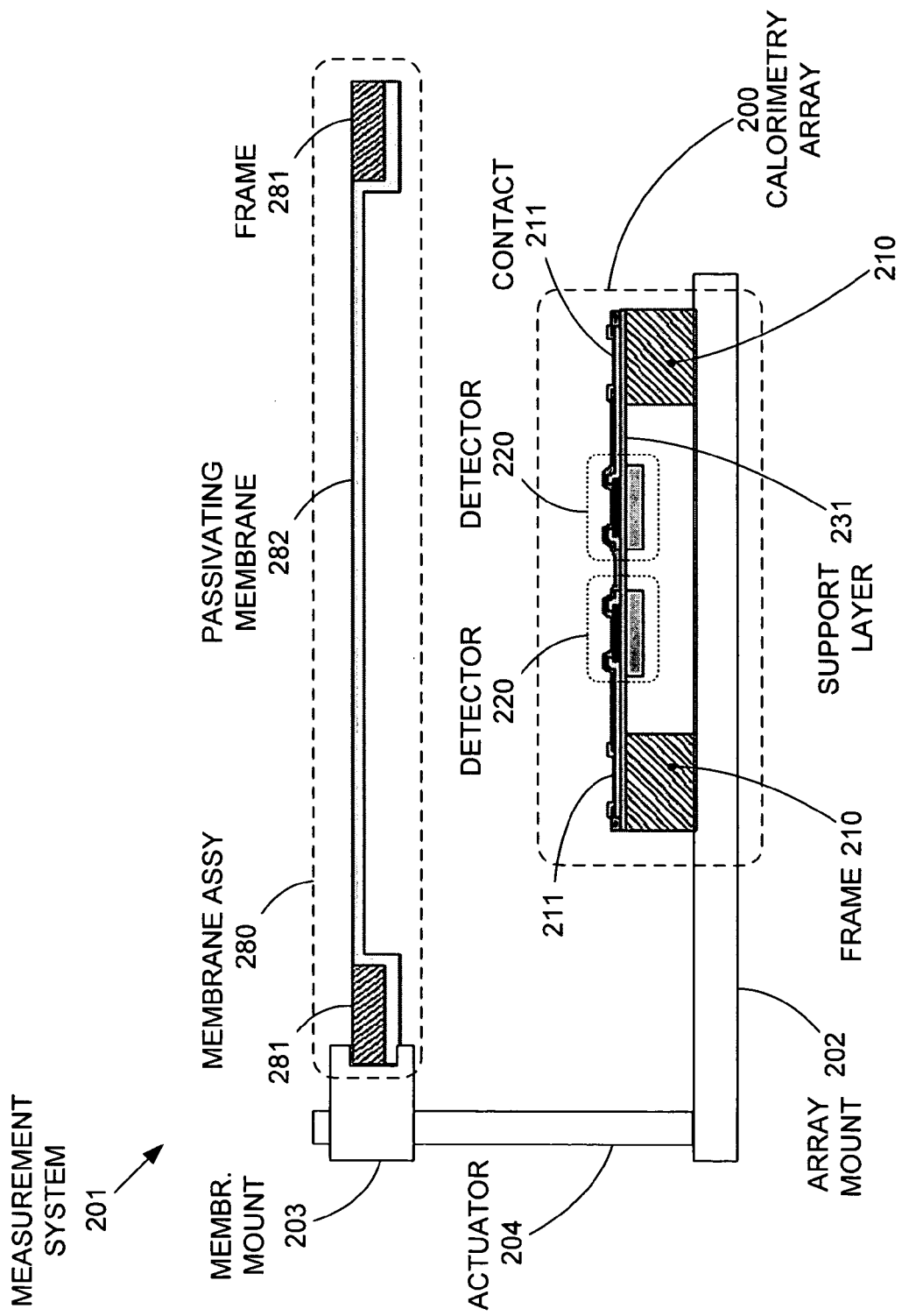
FIGS. 2A and 2B depict a measurement system in accordance with an embodiment of the invention.

FIG. 2A shows a measurement system 201 that includes a replaceable passivating membrane 282, in accordance with an embodiment of the invention. Measurement system 201 includes an array mount 202 for supporting a measurement array 200, a membrane mount 203 for supporting a membrane assembly 280, and an actuator mechanism 204 for moving array mount 202 and membrane mount 203 towards and away from each other.

Measurement array 200 includes multiple detectors 220 formed on a support layer 231, which is in turn supported by a frame 210. Support layer 231 can comprise any material that can maintain detectors 220 in a substantially fixed position relative to frame 210. For example, according to an embodiment of the invention, support layer 210 can comprise a polyimide (e.g., Kapton™) film.

Detectors 220 provide the desired measurement capabilities for measurement array 200. For example, if measurement array 200 comprises a calorimeter array, detectors 220 can comprise thermal sensors for heat measurements. Alternatively, if measurement array 200 comprises a photometric array, detectors 220 can comprise photosensors for radiation measurements.

Note that while two detectors 220 are depicted for exemplary purposes, measurement array 200 can comprise any number of detectors 220. Measurement data from detectors 220 are read out via contacts 211 at the periphery of measurement array 200.

Figure 1A:
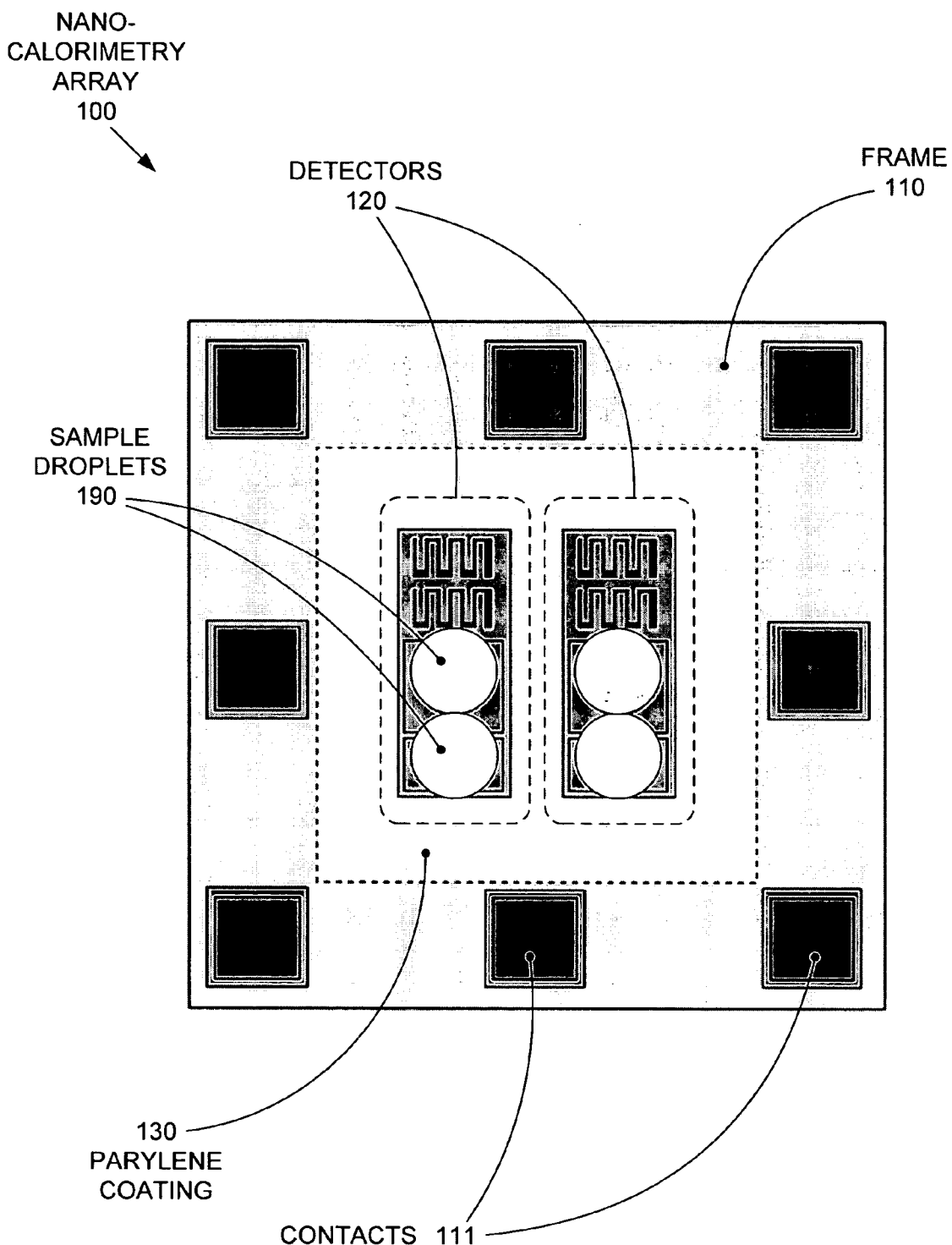
FIG. 1A is a top view of a nanocalorimeter.
Figure 1B:
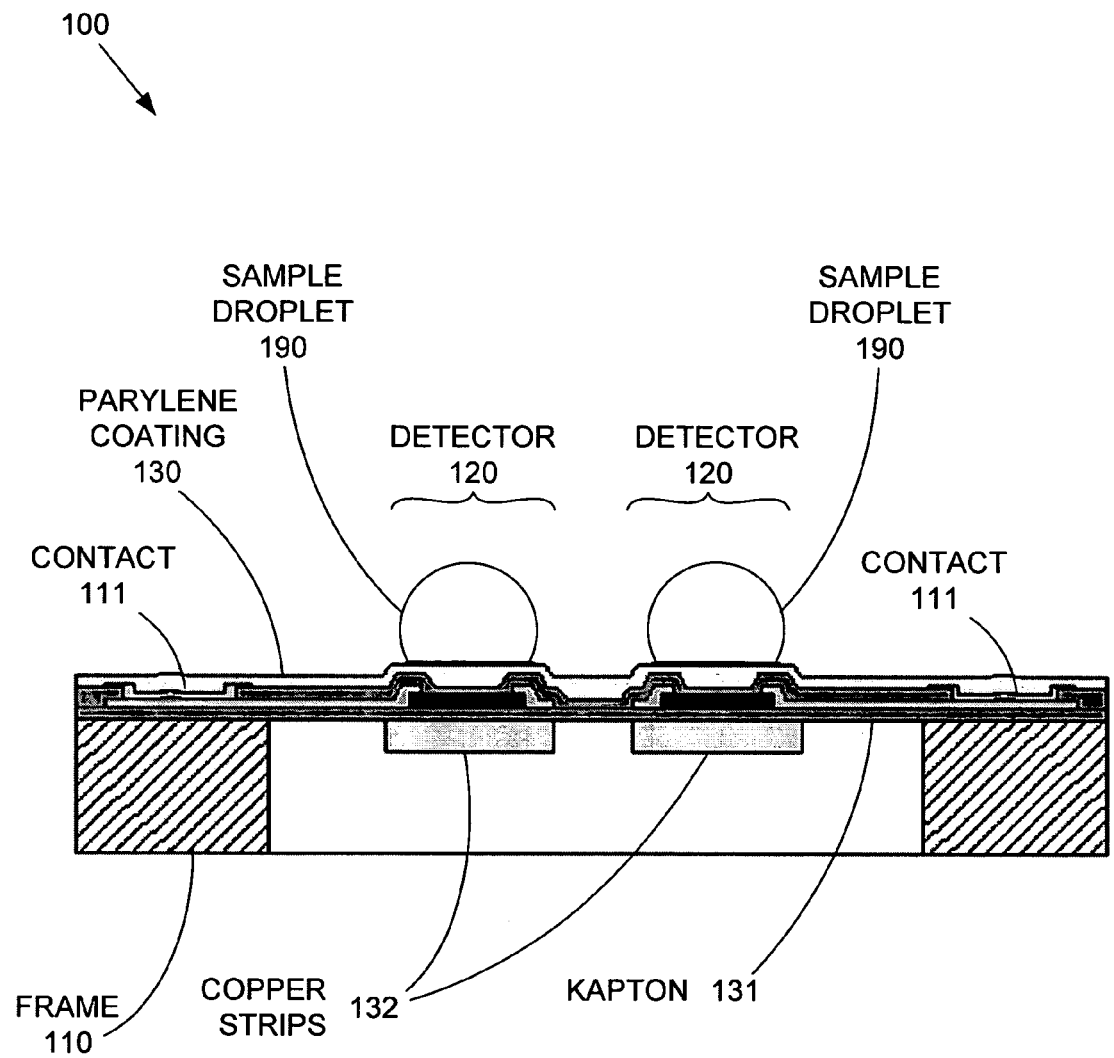
FIG. 1B is a cross section of the nanocalorimeter of FIG. 1A.

Note further that, for exemplary purposes, measurement array 200 is depicted to be substantially similar to nanocalorimeter array 100 shown in FIGS. 1A and 1B, except that measurement array 200 does not include the integral parylene coating 180 of nanocalorimeter array 100. However, as noted above, measurement array 200 can comprise any type of measurement structure.

Passivating membrane 282 is incorporated into a membrane assembly 280 that also includes a support frame 281. Support frame 281 provides a rigid structure that supports the perimeter of passivating membrane 282, thereby maintaining passivating membrane 282 in a substantially planar configuration.

Passivating membrane 282 itself can comprise any flexible material that provides sufficient electrical and chemical passivation against the sample liquids to being measured, while still allowing proper transfer of the measurement parameter of interest. For example, according to an embodiment of the invention, passivating membrane 282 can be a 1-3 μm thick parylene membrane for nanocalorimetry measurements.

In FIG. 2A, membrane mount 203 holds membrane assembly 280 above measurement array 200, so that passivation membrane 282 is facing detectors 220. Then, in FIG. 2B, actuator 204 moves membrane mount 203 towards array mount 202 (as indicated by the arrow). This presses measurement array 200 into passivation membrane 282, so that membrane 282 covers detectors 220 (e.g., stretched over detectors 220). In this manner, membrane 282 effectively becomes a temporary passivation layer for measurement array 200.

Consequently, when sample droplets 290 are subsequently deposited onto passivating membrane 282, detectors 220 are chemically and electrically isolated from those sample droplets 290. Meanwhile, the thermal characteristics of sample drops 290 (e.g., heat of reaction) are transmitted through passivating membrane 220 and can therefore be measured by detectors 220. The measurement data from detectors 220 can then be read out from contacts 211.

According to an embodiment of the invention, a preformed contact opening 204 can be included in passivating membrane 282 at the location of each contact 211 to provide electrical access. According to another embodiment of the invention, a contact pin 205 can be used at each contact 211 to pierce passivating membrane 282. According to another embodiment of the invention, electrical connectivity can be achieved through the edges or backside of frame 210.

According to an embodiment of the invention, measurement array 200 can have a slightly "bowed" (convex) configuration, such that the first contact with passivating membrane 282 is made towards the center of measurement array 200. The contact area between passivating membrane 282 and measurement array 200 will then propagate outward to minimize the chances of air pocket formation between passivating membrane 282 and measurement array 200.

Once the calorimetry measurement operation is complete, actuator 204 can move membrane mount 203 away from array mount 202, thereby lifting passivating membrane 282 off of measurement array 200. The used membrane assembly 280 in membrane mount 203 can then be replaced with a new membrane assembly, and another measurement operation can immediately be performed by measurement system 201.

In this manner, multiple measurement operations can be performed in rapid succession. In addition, because the expensive measurement array 200 can be re-used, the cost of those measurements can be significantly reduced over conventional (single use) systems. Furthermore, the precision and capabilities of measurement array 200 can be increased, since the higher cost associated with those performance enhancements can be offset by the fact that measurement array 200 can be re-used.

Figure 2B:
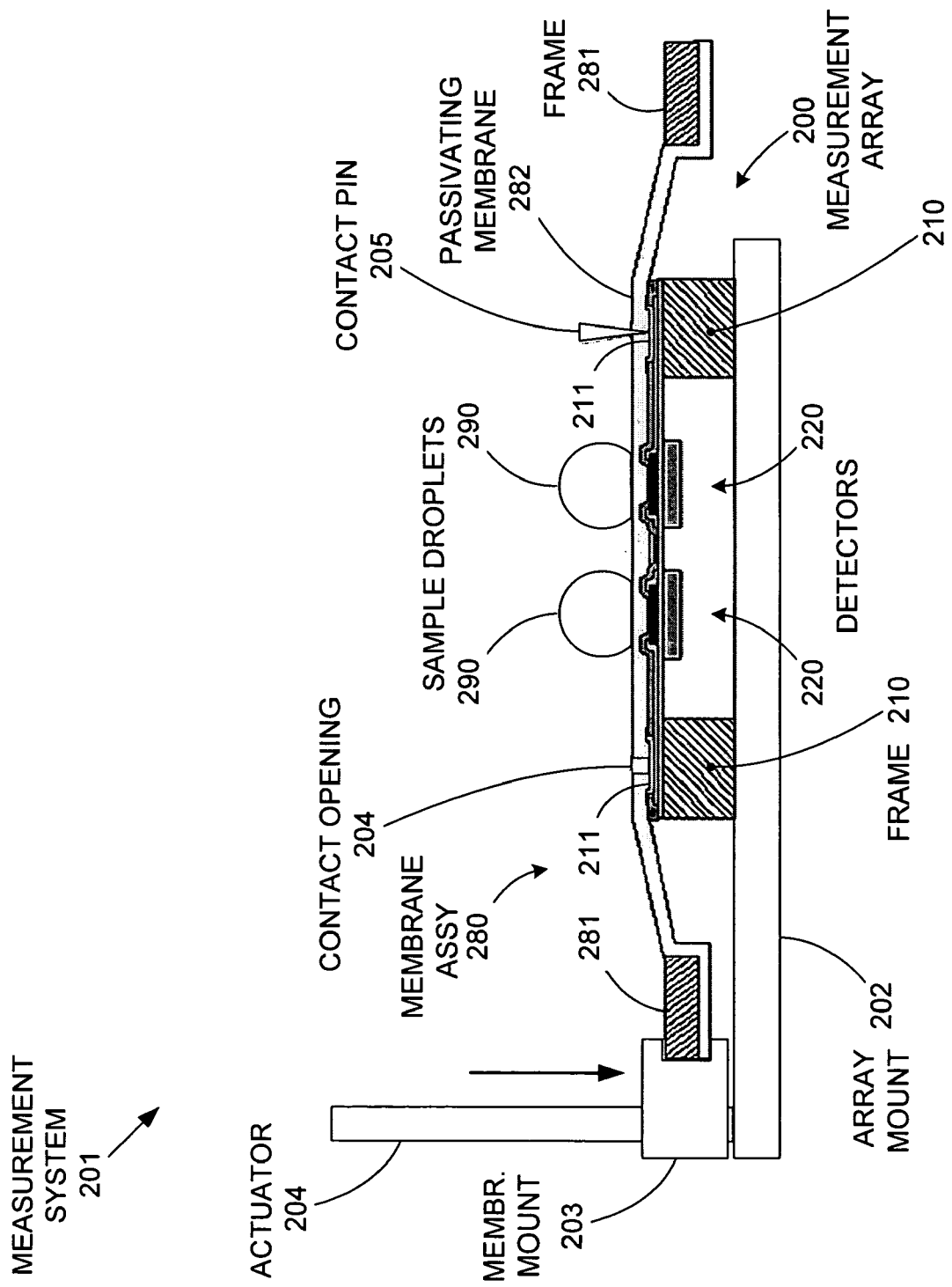
Figure 3:
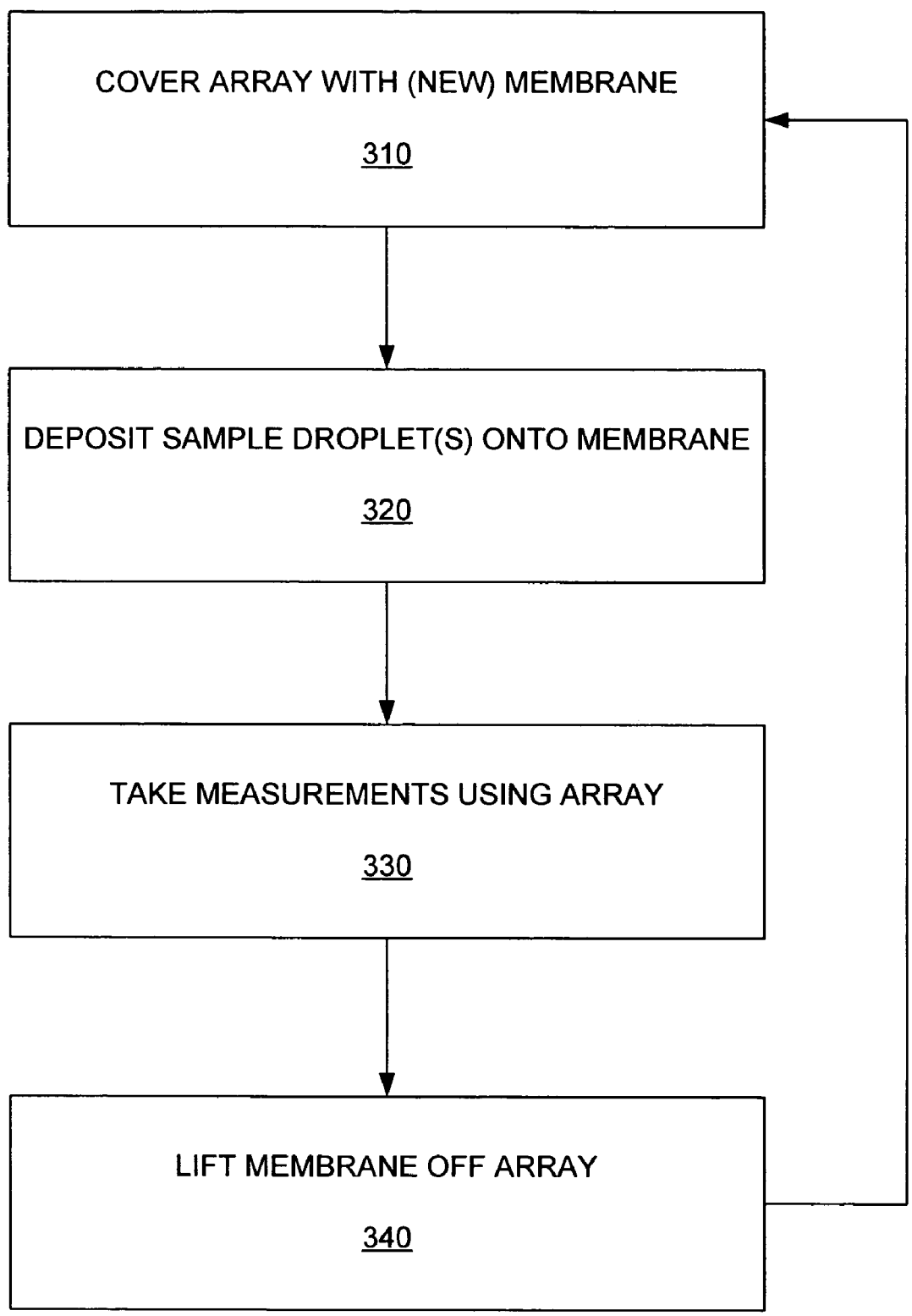
FIG. 3 is a flow diagram of a calorimetry operation performed in accordance with an embodiment of the invention.

FIG. 3 shows a flow chart depicting a calorimetry measurement process in accordance with an embodiment of the invention (such as described with respect to FIGS. 2A and 2B). In a "COVER ARRAY WITH MEMBRANE" step 310, a passivating membrane (e.g., passivating membrane 280) is used to cover the detectors (e.g., detectors 220) of a measurement array (e.g., measurement array 200). Then, when sample droplets (e.g., sample droplets 290) are placed on the passivating membrane in a "DEPOSIT SAMPLE DROPLET(S) ONTO MEMBRANE" step 320, the passivating membrane prevents unwanted chemical and/or electrical interactions between those sample droplets and the detectors of the measurement array.

At the same time, because the passivating membrane is pressed tightly against the detectors of the calorimeter array, measurements (e.g., enthalpic or photometric measurements) can be taken by the detectors in a "TAKE MEASUREMENTS USING ARRAY" step 330. Once the measurement operation complete, the passivating membrane is removed from the measurement array in a "LIFT MEMBRANE OFF ARRAY" step 340. If another measurement is to be taken, the process loops back to step 310, where a new passivating membrane is placed over the measurement array.

Figure 4A:
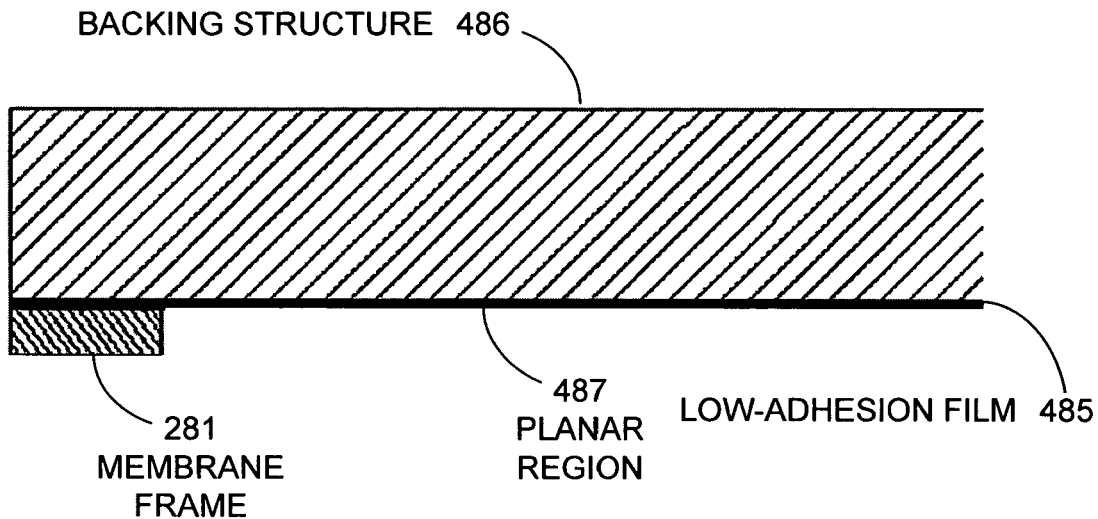
FIGS. 4A, 4B, and 4C depict a method for forming a disposable passivation membrane, in accordance with an embodiment of the invention.
Figure 4B:
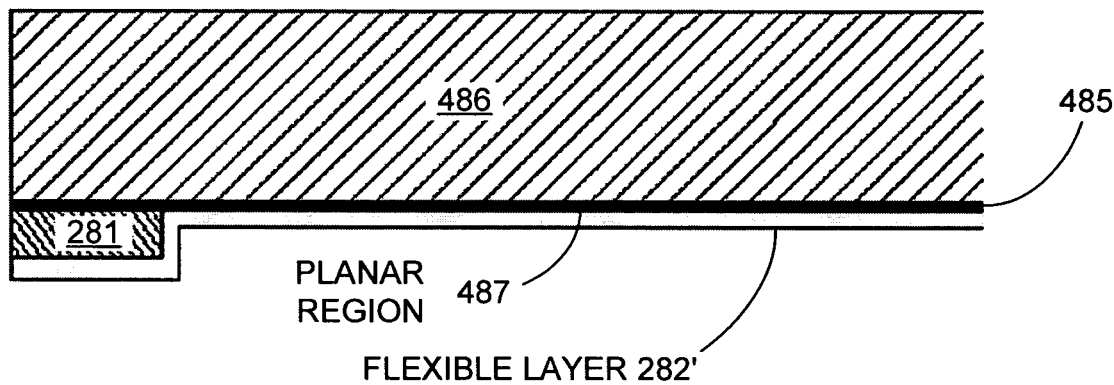
Figure 4C:
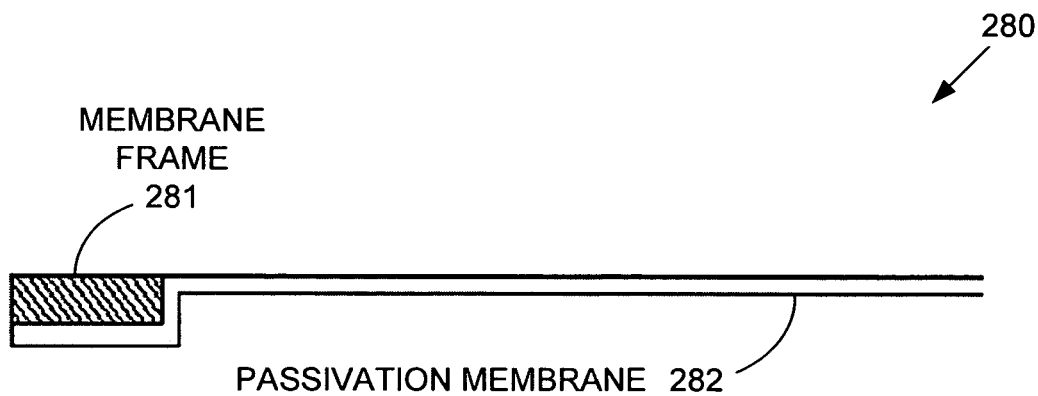

As described with respect to FIGS. 2A and 2B, the passivating membrane can be pre-mounted on a frame (membrane assembly 280) to simplify the step of placing the membrane onto the calorimeter array (step 310). FIGS. 4A-4C depict a method for creating such a mounted membrane, in accordance with an embodiment of the invention. In FIG. 4A, a backing structure 486 is clamped on to a membrane frame 281. Backing structure includes a planar region 487 that is enclosed by frame 281.

Planar region 487 is formed by a low-adhesion film 485, which can be any material that can be readily separated from the desired passivation membrane material. For example, according to various embodiments of the invention, low-adhesion film 485 can be a non-stick surface (e.g., Teflon™), a thermal or UV (ultra-violet) release tape (e.g., Revalpha™ from Nitto Denko Corp.), or even a sacrificial layer that can be dissolved by an appropriate etchant.

In FIG. 4B, a flexible layer 282' of the desired membrane material is formed over planar region 487 and the portion of membrane frame 281 that surrounds planar region 487. The specific means by which flexible layer 282' is formed will depend on the desired membrane material. For example, according to an embodiment of the invention, flexible layer 282' can be created by vapor-depositing parylene over planar region 487 and the surrounding portions of frame 281.

Finally, in FIG. 4C, flexible layer 282' and membrane frame 281 are released from backing structure 486 to create a membrane assembly 280 in which passivating membrane 282 is supported by frame 281. As noted above, this release operation can be performed in a variety of ways, depending on the nature of low-adhesion film 485. According to an embodiment of the invention, a mechanical peel operation can be used to separate membrane 282 from low-adhesion film 485. According to another embodiment of the invention, thermal or UV radiation could be used to reduce the adhesion provided by low-adhesion film 485. According to another embodiment of the invention, a gas or liquid etchant could be used to dissolve low-adhesion film 485.

Although the present invention has been described in connection with several embodiments, it is understood that this invention is not limited to the embodiments disclosed, but is capable of various modifications that would be apparent to one of ordinary skill in the art. For example, rather than forming a membrane via vapor deposition (as described with respect to FIGS. 4A-4C), membrane assembly 280 could be created by affixing a pre-existing sheet of the desired material to a frame. Furthermore, passivation membrane 282 could be placed over measurement array 200 without the use of a membrane frame 281; e.g., by providing a roll of thin parylene sheet and unrolling an appropriate portion over a calorimeter array. In addition, the replaceable passivation layer can be used with any type of measurement array that requires chemical and/or electrical passivation. For example, a clear passivation membrane could be used with a photometric array to provide environmental protection without interfering with the operation of the light sensors. Therefore, the invention is limited only by the following claims and their equivalents.

The invention claimed is:

1. A method for performing a measurement operation, the method comprising:
   covering a measurement array with a first replaceable passivating membrane, wherein the measurement array comprises a plurality of detectors, wherein the first replaceable passivating membrane is mounted on a membrane frame, and wherein said covering comprises placing said membrane frame such that said first replaceable passivating membrane is placed over the plurality of detectors;
   depositing a first plurality of sample droplets onto the first replaceable passivating membrane over the plurality of detectors; and
   taking a first set of measurements from the first plurality of sample droplets using the plurality of detectors.

2. The method of claim 1, wherein the membrane frame supports the first replaceable passivating membrane in a substantially planar configuration, and
   wherein covering the measurement array with the first replaceable passivating membrane further comprises:
   positioning the membrane frame such that the first replaceable passivating membrane faces the plurality of detectors; and
   moving the membrane frame and the calorimeter array towards each other to press the plurality of detectors into the first replaceable passivating membrane, such that the first replaceable passivating membrane is stretched over the plurality of detectors.

3. The method of claim 1, wherein the measurement array comprises a calorimeter array, and
   wherein the first replaceable passivating membrane comprises parylene.

4. A measurement system comprising:
   a measurement array comprising a plurality of detector elements;
   a base structure for supporting the measurement array;
   a mounting structure for supporting a membrane assembly, the membrane assembly comprising a passivating membrane mounted on a rigid frame; and
   an actuating mechanism for changing a distance between the base structure and the mounting structure.

5. The measurement system of claim 4, wherein the measurement array comprises a support structure for supporting the plurality of detector elements, wherein the support structure has a convex shape.

6. The measurement system of claim 4, wherein the measurement array comprises a calorimeter array.

7. The measurement system of claim 4, wherein the measurement array further comprises a plurality of contacts for reading measurement data from the plurality of detector elements.

8. The measurement system of claim 7, further comprising a plurality of contact pins, each of the contact pins being positioned over one of the plurality of contact, and each of the contact pins being sharp enough to pierce the passivating membrane.

* * * * *